(12) United States Patent
Dürrenberger et al.

(10) Patent No.: US 10,617,431 B2
(45) Date of Patent: Apr. 14, 2020

(54) SYSTEMS AND APPARATUS FOR PROVIDING MOTOR PROTECTION IN A POWER TOOL AND METHOD OF MANUFACTURING THE SAME

(75) Inventors: Urs Dürrenberger, Arlesheim (CH); Martin Münch, Liestal (CH); Nils Schmuckli, Sissach (CH)

(73) Assignee: DePuy Synthes Products, Inc., Raynham, MA (US)

( * ) Notice: Subject to any disclaimer, the term of this patent is extended or adjusted under 35 U.S.C. 154(b) by 844 days.

(21) Appl. No.: 13/533,446

(22) Filed: Jun. 26, 2012

(65) Prior Publication Data
US 2013/0340553 A1    Dec. 26, 2013

(51) Int. Cl.
| | |
|---|---|
| *A61B 17/00* | (2006.01) |
| *A61B 17/16* | (2006.01) |
| *A61B 17/14* | (2006.01) |
| *A61B 17/88* | (2006.01) |
| *A61B 17/32* | (2006.01) |

(52) U.S. Cl.
CPC ........ *A61B 17/162* (2013.01); *A61B 17/1622* (2013.01); *A61B 17/1697* (2013.01); *A61B 17/14* (2013.01); *A61B 17/1628* (2013.01); *A61B 17/8875* (2013.01); *A61B 2017/00398* (2013.01); *A61B 2017/320024* (2013.01); *Y10T 29/49826* (2015.01); *Y10T 74/19642* (2015.01)

(58) Field of Classification Search
CPC ........................ A61B 17/1622; A61B 17/1624
See application file for complete search history.

(56) References Cited

U.S. PATENT DOCUMENTS

| | | | |
|---|---|---|---|
| 3,120,845 A | * | 2/1964 | Horner ............... A61B 17/1624 173/217 |
| 5,133,729 A | | 7/1992 | Sjostrom |
| | | (Continued) | |

FOREIGN PATENT DOCUMENTS

| | | | | |
|---|---|---|---|---|
| CN | 1430576 | | 7/2003 | |
| EP | 1122472 A2 | * | 8/2001 | ............. F16J 15/164 |
| | (Continued) | | | |

OTHER PUBLICATIONS

Synthes Small Battery Drive User's Manual, copyright 2002.*
(Continued)

*Primary Examiner* — Victor L MacArthur
(74) *Attorney, Agent, or Firm* — Meunier Carlin & Curfman LLC

(57) ABSTRACT

Systems and apparatus for reliably sealing a surgical device are disclosed herein. Specifically, a surgical device including a drive shaft tube that is coupled to a drive shaft is disclosed. Because the drive shaft tube is coupled to the drive shaft, the drive shaft tube rotates at the same rotational speed as the drive shaft, which is less than the rotational speed of a cannulated motor shaft. The drive shaft tube can extend through the cannulated motor shaft. In addition, a sealing member can be provided to seal between the drive shaft tube (which rotates slowly) and the motor instead of between the motor shaft (which rotates more quickly) and the motor. The sealing member can be provided in a gap defined between an outer surface of a portion of the drive shaft tube extending beyond the cannulated motor shaft and the motor.

13 Claims, 4 Drawing Sheets

(56) References Cited

U.S. PATENT DOCUMENTS

| | | | |
|---|---|---|---|
| 5,207,697 A * | 5/1993 | Carusillo | A61B 17/1626 320/115 |
| 6,497,260 B2 | 12/2002 | Hennan et al. | |
| 6,958,071 B2 | 10/2005 | Carusillo et al. | |
| 7,237,990 B2 * | 7/2007 | Deng | A61B 17/32002 279/79 |
| 9,592,087 B2 | 3/2017 | Brunnett et al. | |
| 2004/0092991 A1 | 5/2004 | Deng | |
| 2007/0021752 A1 | 1/2007 | Rogers | |
| 2010/0262127 A1 * | 10/2010 | Schmied | A61B 17/1624 606/1 |
| 2012/0086227 A1 | 4/2012 | Streater, Jr. et al. | |

FOREIGN PATENT DOCUMENTS

| | | |
|---|---|---|
| EP | 1122472 | 4/2006 |
| JP | H62-236686 | 10/1987 |
| JP | H04-244148 | 9/1992 |
| JP | 2006-507031 | 3/2006 |
| JP | 2010-046269 | 3/2010 |
| JP | 2010-528775 | 8/2010 |
| JP | 2012017827 | 1/2012 |
| JP | 2012017827 A * | 1/2012 |
| WO | 2001/067970 | 9/2001 |

OTHER PUBLICATIONS

Synthes, Small Battery Drive User's Manual, (2000) U.S.

Extended European Search Report, dated Sep. 13, 2013, in connection with corresponding European Application No. 13173767.8.

First Office Action, dated Jan. 14, 2016, received in connection with CN Application No. 201310258181.3 (and English Translation).

Office Action, dated Jan. 30, 2018, received in connection with corresponding JP Patent Application No. 2013-132341 (and English translation).

Decision to grant Japanese Application No. 2013-132341, dated Dec. 18, 2018.

Written Amendment, Claims, Written request/demand for appeal/trial, filed in Japanese Application No. 2013-132341, dated Nov. 15, 2018.

Examination Report dated Dec. 13, 2019, issued in related IN Application No. 1867/DEL/2013, 7 pages.

* cited by examiner

SYSTEMS AND APPARATUS FOR PROVIDING MOTOR PROTECTION IN A POWER TOOL AND METHOD OF MANUFACTURING THE SAME

BACKGROUND

Reliable sealing of power tools used in a medical environment (i.e., surgical power tools) is critical. For example, reliable sealing is necessary to ensure sterility of the power tools. In particular, liquids such as bodily fluids must be prevented from leaking into the internal components of the power tools to prevent contaminating patients. Additionally, reliable sealing is necessary to ensure reliability of the power tools. During sterilization in an autoclave, the power tools are exposed to high temperatures and pressures. Thus, reliable sealing is needed to prevent moisture from leaking into the internal components of the power tools to prevent damage, especially to electrical components.

There are various drive configurations for power tools used in a medical environment. In some configurations, the power tools have in-line motor and drive shafts. In other words, the motor and drive shafts share a common rotation axis. This is shown in FIG. 4, where the motor 402 drives a motor shaft 406, which is communicatively connected to the drive shaft 408 through a gear box device 404. As shown in FIG. 4, the motor shaft 406 and the drive shaft 408 share a common rotation axis 401. In addition, the power tools are often required to accommodate K-wires, which are typically longer than the power tools themselves. Accordingly, the motor and drive shafts are cannulated or have hollow channels to accommodate the K-wires.

In order to prevent fluid from leaking into the internal components (such as the motor 402), the power tools are provided with lip seals 412A and 412B between the motor shaft 406 and the stator. The lip seals 412A and 412B are provided at opposite ends of the motor shaft 406. Additionally, because the motor shaft 406 and the drive shaft 408 rotate at different rotational speeds, a gap is provided between the motor shaft 406 and the drive shaft 408. The lip seal 412B prevents fluid from leaking into the gap.

It is difficult to provide reliable sealing in the power tools when providing lip seals against the motor shaft. In particular, the motor shaft is typically configured to rotate at high speeds (>15,000 RPM, for example) in order to provide the desired output power. The reliability and sealing performance of lip seals, however, depends on the circumferential speed of the motor shaft. Accordingly, the reliability of the lip seals is degraded at higher speeds. Additionally, power loss increases over-proportionally with the circumferential speed of the motor shaft. Thus, reliable sealing of power tools is needed.

SUMMARY

Systems and apparatus for providing motor protection in a power tool are disclosed herein. The systems and apparatus can be used to reliably seal a surgical device. Specifically, a surgical device including a drive shaft tube that is coupled to a drive shaft is disclosed. Because the drive shaft tube is coupled to the drive shaft, the drive shaft tube rotates at the same rotational speed as the drive shaft, which is less than the rotational speed of a cannulated motor shaft. The drive shaft tube can extend through the cannulated motor shaft. In addition, a sealing member can be provided to seal between the drive shaft tube (which rotates more slowly) and the motor instead of between the motor shaft (which rotates more quickly) and the motor. For example, the sealing member can be provided in a gap defined between an outer surface of a portion of the drive shaft tube extending beyond the cannulated motor shaft and the motor housing.

For example, a surgical device according to one implementation of the invention can include: a motor having a cannulated motor shaft; a gear box device; a drive shaft; a drive shaft tube and a sealing member. The drive shaft can be communicatively connected to the cannulated motor shaft through the gear box device. The drive shaft can extend distally from the gear box device and the cannulated motor shaft can extend distally to the gear box device. In addition, the cannulated motor shaft and the drive shaft can have a common rotation axis. Additionally, the drive shaft tube can be coupled to the drive shaft and extend proximally from the gear box device through the cannulated motor shaft and beyond the proximal end of the cannulated motor shaft. The sealing member can be arranged adjacent to the proximal end of the cannulated motor shaft and provide a seal between the drive shaft tube and the motor.

Optionally, the surgical device can include a support member arranged adjacent to the proximal end of the cannulated motor shaft. The drive shaft tube can be mounted on the support member such that a space is provided between the drive shaft tube and the cannulated motor shaft. For example, the support member can be a ball bearing.

In some implementations, the gear box device can be configured to convert a higher rotational speed of the cannulated motor shaft to a lower rotational speed of the drive shaft.

Additionally, the drive shaft tube can be coupled to the drive shaft such that the drive shaft tube is configured to rotate at the lower rotational speed of the drive shaft. Alternatively, the drive shaft tube and the drive shaft can be formed from a single piece of material such that the drive shaft tube is configured to rotate at the lower rotational speed of the drive shaft.

In addition, at least a portion of the sealing member can contact an outer surface of the drive shaft tube. For example, the sealing member can include a concentric ring and a lip. The lip can extend radially from the concentric ring, the concentric ring can be disposed around an outer surface of the drive shaft tube, and at least a portion of the lip can contact the outer surface of the drive shaft tube.

In some implementations, the surgical device can include a motor housing supporting the motor. A gap can be provided between an inner surface of a proximal portion of the motor housing and the outer surface of the drive shaft tube, and at least one of the sealing member and the support member can be disposed in the gap.

In another implementation, a sealing system for use with a surgical device can include: an elongate drive shaft tube coupled to a drive shaft that extends through a cannulated motor shaft; and a sealing member disposed in contact with at least a portion of the elongate drive shaft tube. In addition, the elongate drive shaft tube can be configured to rotate at a rotational speed of the drive shaft.

Optionally, the cannulated motor shaft can have proximal and distal ends, at least a portion of the elongate drive shaft tube can extend beyond the proximal end of the cannulated motor shaft, and the sealing member can be disposed in contact with the portion of the elongate drive shaft tube extending beyond the proximal end of the cannulated motor shaft.

In some implementations, the rotational speed of the drive shaft can be less than or equal to approximately 3,000 RPM.

Additionally, the elongate drive shaft tube can be integrally coupled to the drive shaft.

Alternatively or additionally, the elongate drive shaft tube and the drive shaft can be formed from a single piece of material.

For example, the sealing member can include a concentric ring and a lip. The lip can extend radially from the concentric ring, the concentric ring can be disposed around an outer surface of the drive shaft tube, and at least a portion of the lip can contact the outer surface of the drive shaft tube.

In yet another implementation, a method of manufacturing a surgical device can include: providing a motor comprising a cannulated motor shaft; providing a gear box device; providing a drive shaft; and providing a sealing member. The drive shaft can be communicatively connected to the cannulated motor shaft through the gear box device. The drive shaft can extend distally from the gear box device and the cannulated motor shaft can extend distally to the gear box device. In addition, the cannulated motor shaft and the drive shaft can have a common rotation axis. Additionally, the drive shaft tube can be coupled to the drive shaft and extend proximally from the gear box device through the cannulated motor shaft and beyond the proximal end of the cannulated motor shaft. The sealing member can be arranged adjacent to the proximal end of the cannulated motor shaft and provide a seal between the drive shaft tube and the motor.

The method can also include providing a support member adjacent to the proximal end of the cannulated motor shaft. The drive shaft tube can be mounted on the support member such that a space is provided between the drive shaft tube and the cannulated motor shaft.

In some implementations, the gear box device can be configured to convert a higher rotational speed of the cannulated motor shaft to a lower rotational speed of the drive shaft.

In addition, at least a portion of the sealing member can contact an outer surface of the drive shaft tube. For example, the sealing member can include a concentric ring and a lip. The lip can extend radially from the concentric ring, the concentric ring can be disposed around an outer surface of the drive shaft tube, and at least a portion of the lip can contact the outer surface of the drive shaft tube.

In some implementations, the method can include providing a motor housing supporting the motor. A gap can be provided between an inner surface of a proximal portion of the motor housing and the outer surface of the drive shaft tube, and at least one of the sealing member and the support member can be disposed in the gap.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. While implementations will be described for providing a reliable seal in a surgical power tool, it will become evident to those skilled in the art that the implementations are not limited thereto but may also be applicable to other types of power tools.

Figure 1:
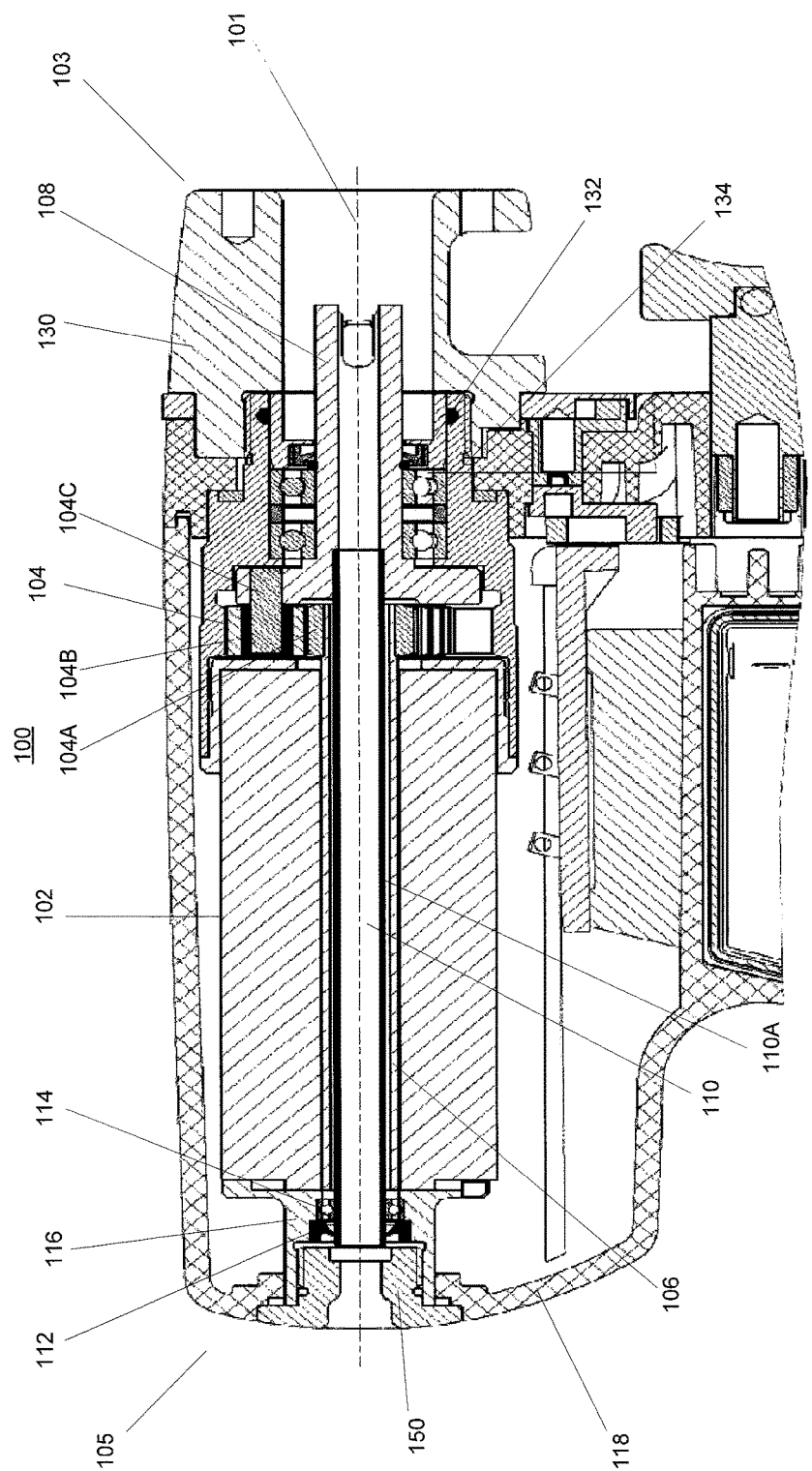
FIG. 1 illustrates a cross-sectional view of a surgical device.
Figure 2:
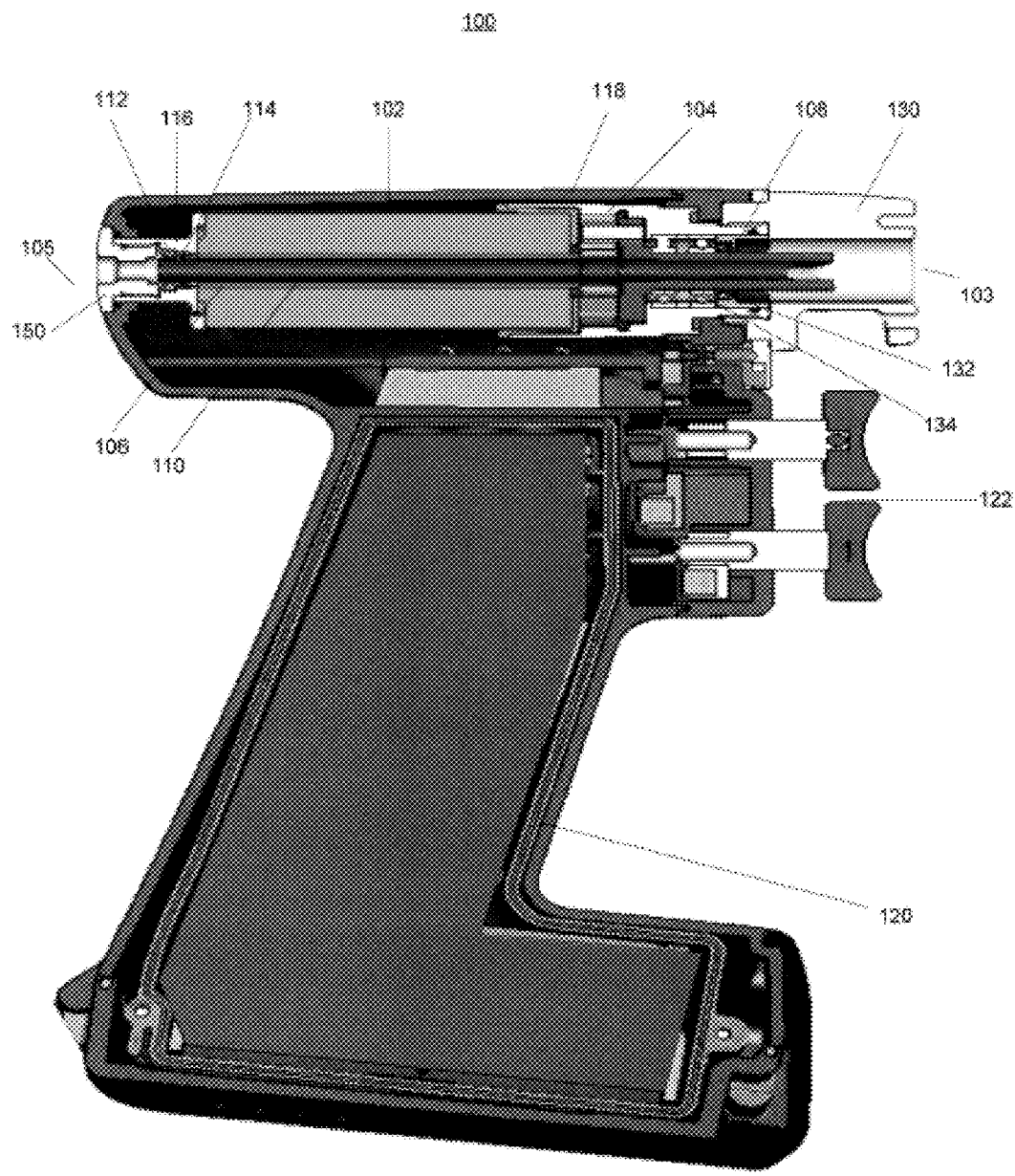
FIG. 2 illustrates another cross-sectional view of the surgical device.

Referring now to FIGS. 1 and 2, cross sectional views of a surgical device 100 are shown. The surgical device 100 is a power tool used during various surgical procedures. The surgical device 100 has a proximal end 105 and a distal end 103, and the surgical device 100 has a device casing 118 that houses the internal components. The surgical device 100 includes a motor 102. The motor 102 includes a motor housing 116 supporting the motor 102 and an elongate motor shaft 106. The motor housing 116 is stationary, and the motor shaft 106 is capable of rotating. As shown in FIGS. 1 and 2, a proximal portion of the motor housing 116 accommodates an end piece 150. The end piece 150 holds the device casing 118 in place. For example, the end piece 150 can be screwed into the motor housing 116. In the implementations discussed herein, the motor 102 can be any type of electric motor operable to drive surgical tools. It should be understood that the characteristics of the motor 102 can be selected based on the desired operating characteristics of the surgical device 100. One or more surgical tool attachments such as surgical drills, saws, etc., for example, can be attached to the surgical device 100 through the coupling head 130. In some implementations, the coupling head 130 can accommodate additional drive attachments that accommodate the surgical tools. For example, the additional drive attachments can convert/transfer motive force to the surgical tools. In addition, the surgical device 100 is operable to drive K-wires. In particular, a K-wire attachment that accommodates K-wires can be attached to the surgical device 100 through the coupling head 130. As shown in FIG. 2, an operator can grip the surgical device 100 by the handle 120 and operate the motor 102 using triggers 122. For example, one of the triggers 122 can cause the motor 102 to rotate in a first direction (i.e., a forward direction) and another one of the triggers 122 can cause the motor 102 to rotate in a second direction (i.e., a backward direction).

The motor 102 includes the elongate motor shaft 106, which is communicatively connected to an elongate drive shaft 108 through a gear box device 104. As shown in FIGS. 1 and 2, the motor shaft 106 extends distally through the motor 102 to the gear box device 104. The gear box device 104 is configured to convert and transfer the rotational speed and torque of the motor shaft 106 to the drive shaft 108. Typically, a motor suitable for use in a surgical power tool is required to be relatively small and lightweight. It should be understood that smaller, lighter and more powerful motors require higher speeds. Therefore, the motor 102 rotates at a higher rotational speed than the desired rotational speed of the attachable surgical tools in order to achieve the desired output torque, and the gear box device 104 can be used to convert and transfer the rotational speed and torque of the motor shaft 106 to the drive shaft 108. For example, in some implementations, the motor shaft 106 may rotate at approximately 15,000 to 20,000 RPM while the desired rotational speed of the drive shaft 108 may be approximately 3,000 RPM (i.e., 5-6 times slower than the motor shaft 106). Alternatively or additionally, the additional drive attachments can further reduce the rotational speed to the desired rotational speed of the surgical tools, which may be approximately less than or equal to 1,000 RPM. Further, the additional drive attachments can increase the rotational speed to the desired rotational speed of the surgical tools (e.g., 15,000 RPM), which may be approximately greater than the rotational speed of the drive shaft 108, to drive high-speed cutting tools such as burrs, for example. It should be understood that the rotational speeds discussed above for the motor 102, motor shaft 106, drive shaft 108, surgical tools, etc. can be selected based on the desired operating characteristics of the surgical device 100, and therefore, can have other values. For example, the desired rotational speed of the drive shaft 108 can be more or less than 3,000 RPM depending on the desired operating characteristics of the surgical device 100. Thus, the desired rotational speed of the drive shaft 108 is not limited to 3,000 RPM, which is only one example desired rotational speed.

The gear box device 104 can be any type of gear box that is capable of converting and transferring the rotational speed and torque of the motor 102 in one or more steps. For example, the gear box device 104 can be a planetary gear system. For example, the motor shaft 106 can be connected to a sun gear 104A, and the drive shaft 108 can be connected to one or more planetary gears 104B. In some implementations, the drive shaft 108 can be connected with the one or more planetary gears 104B using pin(s) 104C that are pushed through the drive shaft 108 and into one of the planetary gears 104B. Alternatively, the drive shaft 108 can be connected with the one or more planetary gears 104B using pins 104C that are integral with the drive shaft 108. The gear box device 104, therefore, converts a higher rotational speed of the motor shaft 106 to a lower rotational speed of the drive shaft 108. Additionally, the gear box device 104 transfers torque from the motor shaft 106 to the drive shaft 108. In some implementations, a lower torque of the motor shaft 106 is converted to a higher torque and transferred to the drive shaft 108.

As shown in FIGS. 1 and 2, the motor shaft 106 and the drive shaft 108 are in-line. Additionally, the motor shaft 106 extends distally through the motor 102 to the gear box device 104, and the drive shaft 108 extends distally from the gear box device 104. In the implementations discussed herein, the motor shaft 106 and the drive shaft 108 are coaxial, or share a common rotation axis 101, for example. When the motor shaft 106 and the drive shaft 108 are coaxially, the surgical device 100 can be made smaller as compared to the case where the motor shaft 106 and the drive shaft 108 do not share the common rotation axis 101. Additionally, the motor shaft 106 and the drive shaft 108 can be cannulated shafts. In other words, the motor shaft 106 and the drive shaft 108 can have hollow central channels extending through the length of each shaft. As discussed above, the surgical device 100 is operable to drive K-wires, which are typically longer than the surgical device 100 itself. Accordingly, the K-wires can be inserted entirely through the surgical device 100 (i.e., from the distal end 103 to the proximal end 105), exiting through the device housing 118 of the surgical device 100.

A drive shaft tube 110 can be coupled to the drive shaft 108. The drive shaft tube 110 can extend proximally from the gear box device 104. For example, the drive shaft tube 110 can extend proximally from the gear box device 104 into the motor shaft 106. When the motor shaft 106 is cannulated, the drive shaft tube 110 can extend through the hollow channel of the motor shaft 106. In particular, the drive shaft tube 110 can extend through the motor shaft 106 and beyond a proximal end of the motor shaft 106. For example, a portion of the drive shaft tube 110 can extend proximally beyond the proximal end of the motor shaft 106. As shown in FIGS. 1 and 2, the drive shaft tube 110 extends proximally from the gear box device 104 through an entire length of the motor shaft 106. Similarly to the motor shaft 106 and the drive shaft 108, the drive shaft tube 110 can be cannulated in order to accommodate insertion of the K-wires through the surgical device 100. In addition, the drive shaft tube 110 can share the common rotation axis 101 with the motor shaft 106 and the drive shaft 108.

The drive shaft tube 110 can be coupled to the drive shaft 108 such that the drive shaft tube 110 is capable of rotating at the same rotational speed as the drive shaft 108. In some implementations, the drive shaft tube 110 and the drive shaft 108 are separate pieces that are integrally coupled together, for example, in a location adjacent to the gear box device 104. In other implementations, the drive shaft tube 110 and the drive shaft 108 are a single, integrated piece (i.e., formed from a single piece of material). In both cases discussed above, the drive shaft tube 110 and the drive shaft 108 are capable of rotating at the same rotational speed. In particular, the drive shaft tube 110 is capable of rotating at a lower rotational speed as compared to the motor shaft 106. In addition, the drive shaft tube 110 and the drive shaft 108 are coupled such that there is no gap or space for fluid to leak from the hollow channel of the drive shaft tube 110 and/or the drive shaft 108 to the motor 102. Optionally, a wall thickness of the drive shaft 108 can be greater than a wall thickness of the drive shaft tube 110 because torque is transferred from the motor shaft 106 to the drive shaft 108 while there is essentially no torque on the drive shaft tube 110.

Figure 3A:
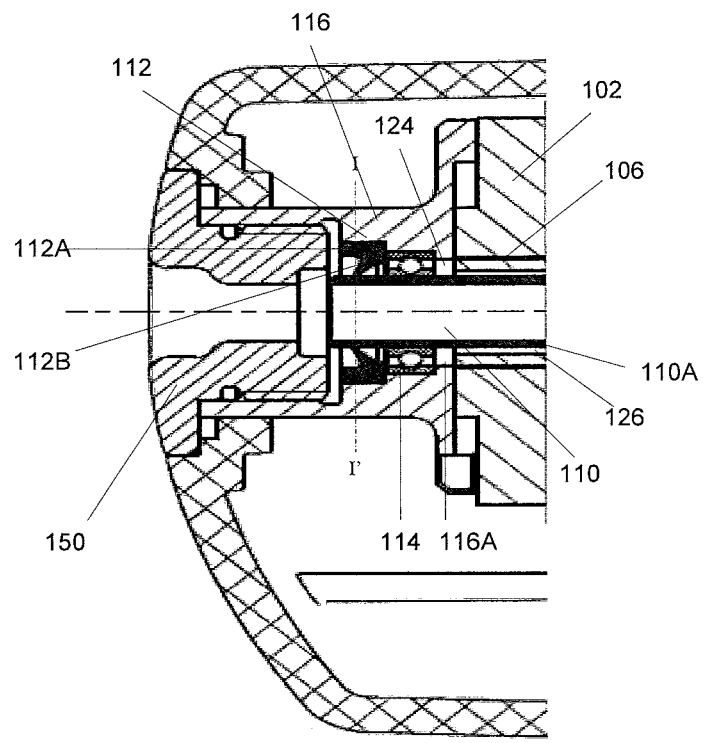
FIG. 3A illustrates a cross-sectional view of a proximal portion of the surgical device of FIGS. 1 and 2.

A sealing member 112 can be provided adjacent to the proximal end of the motor shaft 106 to prevent fluid from leaking into the motor 102. In some implementations, the sealing member 112 can be provided between the motor housing 116 and the drive shaft tube 110. Alternatively, in other implementations, the sealing member 112 can be provided between the end piece 150 and the drive shaft tube 110. Referring now to FIG. 3A, a gap 124 is provided between the proximal portion of the motor housing 116, which is stationary, and the drive shaft tube 110, which is capable of rotating. The gap 124 can be an annular ring surrounding the portion of the drive shaft tube 110 that extends beyond the proximal end of the motor shaft 106. Alternatively, the gap 124 can be a space having any shape surrounding the portion of the drive shaft tube 110 that extends beyond the proximal end of the motor shaft 106. Specifically, the gap 124 is provided between an inner surface 116A of the proximal portion of the motor housing 116 and an outer surface 110A of the drive shaft tube 110. The gap 124 provides a clearance (or space) in which the drive shaft tube 110 can rotate. In order to prevent fluid from leaking through the gap 124, the sealing member 112 can be provided in the gap 124. At least a portion of the sealing member 112 can contact the outer surface 110A of the drive shaft tube 110. The portion of the sealing member 112 contacting the outer surface 110A of the drive shaft tube 110 can extend circumferentially around the entire outer surface 110A of the drive shaft tube 110. For example, the sealing member 112 can be a lip seal, an O-ring, or any other type of seal. The sealing member 112 can be made from any type of material suitable for preventing fluid from leaking into the motor 102 such as rubber (i.e., NBR, Silicone, etc.), for example.

Figure 3B:
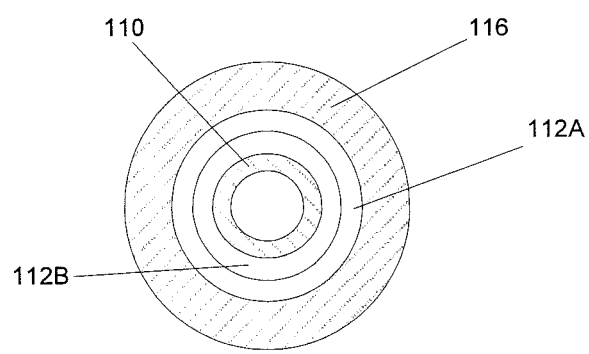
FIG. 3B illustrates a cross-sectional view of the proximal portion of the surgical device along line I-I' of FIG. 3A.
Figure 4:
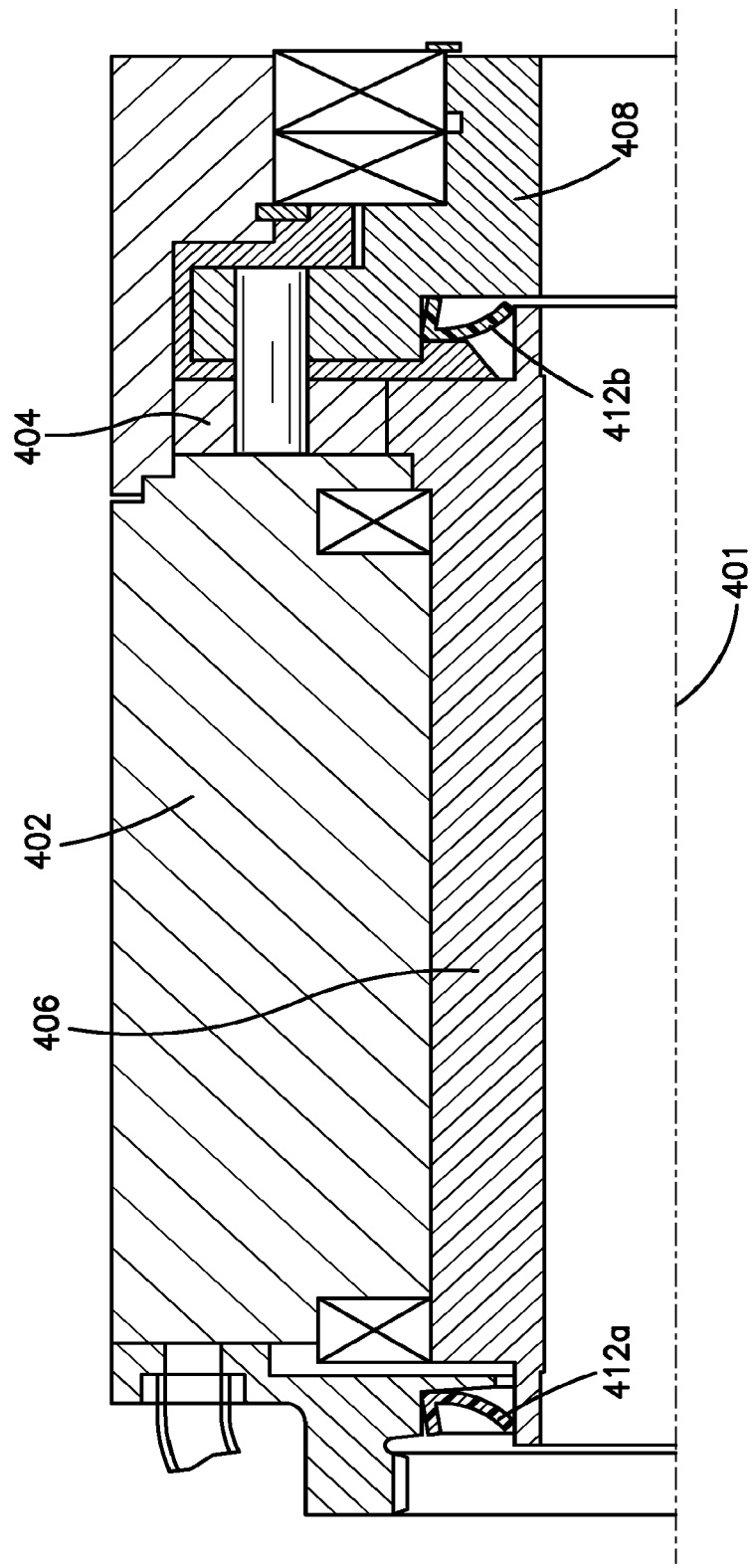
FIG. 4 illustrates a cross-sectional view of a motor shaft in a surgical device in related art.

The sealing member 112 can be provided around the outer surface 110A of the drive shaft tube 110. For example, referring to FIGS. 3A and 3B, the sealing member 112 can have a concentric ring 112A and a lip 112B. The lip 112B can extend radially from the concentric ring 112A, and the lip 112B can be tapered from the concentric ring 112A. By tapering the lip 112B, the portion of the lip 112B contacting the outer surface 110A of the drive shaft tube 110 can be reduced. The concentric ring 112A can be provided around the outer surface 110A of the drive shaft tube 110 such that at least a portion of the lip 112B contacts the outer surface 110A of the drive shaft tube 110. The sealing member 112, therefore, prevents fluid from leaking into the motor 102.

In addition to the sealing member 112, a support member 114 can be provided adjacent to the proximal end of the motor shaft 106. In some implementations, the support member 114 can be provided between the motor housing 116 and the drive shaft tube 110. Alternatively, in other implementations, the support member 114 can be provided between the end piece 150 and the drive shaft tube 110. For example, the support member 114 can be provided in the gap 124, which is provided between the proximal portion of the motor housing 116 and the drive shaft tube 110, and can be disposed between the sealing member 112 and the proximal end of the motor shaft 106. The drive shaft tube 110 can be mounted through the support member 114. The support member 114 provides support for the drive shaft tube 110 so that the drive shaft tube 110 does not contact the motor shaft 106. As discussed above, the motor shaft 106 can rotate at a higher rotational speed than the drive shaft tube 110. Thus, the drive shaft tube 110 and the motor shaft 106 should not come into contact. As shown in FIG. 3A, a space 126 is provided between the drive shaft tube 110 and the motor shaft 106. Specifically, the space 126 is provided between the outer surface 110A of the drive shaft tube 110 and an inner surface of the motor shaft 106. The space 126 can be, for example, an annular ring that extends around the outer surface 110A of the drive shaft tube 110. The support member 114 can be configured to maintain the space 126 between the drive shaft tube 110 and the motor shaft 106. In addition, the support member 114 allows the drive shaft tube 110 to rotate within the support member 114. For example, the support member 114 can be a ball bearing.

Similarly to the sealing member 112 and the support member 114 discussed above (and provided near the proximal end of the surgical device 100), a distal sealing member 132 and a distal support member 134 can be provided near the distal end of the surgical device 100. For example, as shown in FIGS. 1 and 2, the distal sealing member 132 and the distal support member 134 can be provided adjacent to a distal end of the drive shaft 108. The distal sealing member 132 and the distal support member 134 can be provided in a space between stationary components of the surgical device 100 and the drive shaft 108, which can rotate. The distal support member 134, which can be a ball bearing, for example, can provide support for the drive shaft 108 while allowing the drive shaft 108 to rotate within the distal support member 134. In addition, the distal sealing member 132, which can be a lip seal, for example, can prevent fluid from leaking between the drive shaft 108 and the motor 102.

According to the implementations discussed herein, it is possible to provide a more reliable sealing in a surgical device. For example, more reliable sealing is provided because the sealing member seals between the drive shaft tube (which rotates more slowly) and the motor instead of between the motor shaft (which rotates more quickly) and the motor. In addition, it is possible to reduce the number of sealing members needed to protect the motor of the surgical device because an additional sealing member is not required to seal between the motor shaft and the drive shaft. It is also possible to reduce drag moment on the motor because there is less friction present on the slower rotating (and higher torque) drive shaft tube than on the faster rotating (and lower torque) motor shaft. Further, by reducing the speed difference between the K-wire and the drive shaft tube, it is possible to reduce noise and wear on both the K-wire and the rotating shaft.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A surgical device, comprising:
    a motor comprising a cannulated motor shaft, the cannulated motor shaft having proximal and distal ends;
    a motor housing supporting the motor and the cannulated motor shaft;
    an end piece coupled to a proximal end of the motor housing;
    a gear box device within the motor housing;
    a drive shaft communicatively connected to the cannulated motor shaft through the gear box device, the drive shaft extending distally from the gear box device and the cannulated motor shaft extending distally to the gear box device, wherein the cannulated motor shaft and the drive shaft have a common rotation axis;
    a drive shaft tube coupled to the drive shaft that extends proximally from the gear box device through the cannulated motor shaft and beyond the proximal end of the cannulated motor shaft, wherein the drive shaft tube is coupled to the drive shaft such that the drive shaft tube rotates at a same rotational speed as the drive shaft;
    a sealing member arranged adjacent to the proximal end of the cannulated motor shaft and between the motor housing and the drive shaft tube, the sealing member providing a seal between the drive shaft tube and the motor housing, wherein the sealing member comprises a concentric ring and a lip, the lip extending radially from the concentric ring, and the concentric ring being disposed around an outer surface of the drive shaft tube, wherein the lip is tapered from the concentric ring to the outer surface of the drive shaft, and the tapered portion of the lip contacts the outer surface of the drive shaft tube; and
    a support member arranged adjacent to the proximal end of the cannulated motor shaft, wherein the drive shaft tube is mounted on the support member such that the support member provides a space between the drive shaft tube and the cannulated motor shaft.

2. The surgical device of claim 1, wherein the support member is a ball bearing.

3. The surgical device of claim of claim 1, wherein the gear box device is configured to convert a higher rotational speed of the cannulated motor shaft to a lower rotational speed of the drive shaft.

4. The surgical device of claim 1, wherein at least a portion of the sealing member contacts an outer surface of the drive shaft tube.

5. The surgical device of claim 4, wherein a gap is defined between an inner surface of a proximal portion of the motor housing and the outer surface of the drive shaft tube, and at least one of the sealing member and the support member are disposed in the gap.

6. A sealing system for use with a surgical device, the surgical device including a motor, a motor housing supporting the motor and an end piece coupled to a proximal end of the motor housing, the motor having a cannulated motor shaft communicatively connected to a drive shaft through a gear box device, the drive shaft extending distally from the gear box device and the cannulated motor shaft extending distally to the gear box device, the sealing system comprising:
an elongate drive shaft tube coupled to the drive shaft that extends through the cannulated motor shaft, wherein the drive shaft tube is coupled to the drive shaft such that the drive shaft tube rotates at a same rotational speed as the drive shaft;
a sealing member located between the motor housing and the drive shaft tube, the sealing member disposed in contact with at least a portion of the elongate drive shaft tube, wherein the elongate drive shaft tube is configured to rotate at a rotational speed of the drive shaft, wherein the sealing member comprises a concentric ring and a lip, the lip extending radially from the concentric ring, and the concentric ring being disposed around an outer surface of the drive shaft tube, wherein the lip is tapered from the concentric ring to the outer surface of the drive shaft, and the tapered portion of the lip contacts the outer surface of the drive shaft tube; and
a support member arranged adjacent to and abutting the proximal end of the cannulated motor shaft, wherein the drive shaft tube is mounted on the support member such that a space is provided along the entire length between the drive shaft tube and the cannulated motor shaft.

7. The sealing system of claim 6, wherein the cannulated motor shaft has proximal and distal ends, at least a portion of the elongate drive shaft tube extends beyond the proximal end of the cannulated motor shaft, and the sealing member is disposed in contact with the portion of the elongate drive shaft tube extending beyond the proximal end of the cannulated motor shaft.

8. The sealing system of claim 6, wherein the rotational speed of the drive shaft is less than or equal to approximately 3,000 RPM.

9. The sealing system of claim 6, wherein the elongate drive shaft tube is integrally coupled to the drive shaft.

10. The sealing system of claim 9, wherein the elongate drive shaft tube and the drive shaft are formed from a single piece of material.

11. A method of manufacturing a surgical device, comprising:
providing a motor comprising a cannulated motor shaft, the cannulated motor shaft defining proximal and distal ends;
providing a motor housing supporting the motor and the cannulated motor shaft;
providing an end piece coupled to a proximal end of the motor housing;
providing a gear box device within the motor housing;
providing a drive shaft communicatively connected to the cannulated motor shaft through the gear box device, the drive shaft extending distally from the gear box device and the cannulated motor shaft extending distally to the gear box device, wherein the cannulated motor shaft and the drive shaft have a common rotation axis;
providing a drive shaft tube coupled to the drive shaft that extends proximally from the gear box device through the cannulated motor shaft and beyond the proximal end of the cannulated motor shaft, wherein the drive shaft tube is coupled to the drive shaft such that the drive shaft tube rotates at a same rotational speed as the drive shaft;
providing a sealing member adjacent to the proximal end of the cannulated motor shaft and between the motor housing and the drive shaft tube, the sealing member providing a seal between the drive shaft tube and the motor, wherein the sealing member comprises a concentric ring and a lip, the lip extending radially from the concentric ring, and the concentric ring being disposed around an outer surface of the drive shaft tube, wherein the lip is tapered from the concentric ring to the outer surface of the drive shaft, and the tapered portion of the lip contacts the outer surface of the drive shaft tube; and
a support member arranged adjacent to the proximal end of the cannulated motor shaft, wherein the drive shaft tube is mounted on the support member such that a space is provided along the entire length between the drive shaft tube and the cannulated motor shaft.

12. The method of claim 11, wherein the gear box device is configured to convert a higher rotational speed of the cannulated motor shaft to a lower rotational speed of the drive shaft.

13. The method of claim 11, wherein a gap is defined between an inner surface of a proximal portion of the motor housing and the outer surface of the drive shaft tube, and at least one of the sealing member and the support member are disposed in the gap.

* * * * *

UNITED STATES PATENT AND TRADEMARK OFFICE
CERTIFICATE OF CORRECTION

PATENT NO.         : 10,617,431 B2
APPLICATION NO.    : 13/533446
DATED              : April 14, 2020
INVENTOR(S)        : Urs Dürrenberger et al.

It is certified that error appears in the above-identified patent and that said Letters Patent is hereby corrected as shown below:

In the Claims

Claim 6 - Column 9, Line 35, the term "and abutting" should be removed.

Signed and Sealed this
Fourth Day of August, 2020

Andrei Iancu
*Director of the United States Patent and Trademark Office*